US006872573B2

(12) United States Patent
Albarella et al.

(10) Patent No.: US 6,872,573 B2
(45) Date of Patent: Mar. 29, 2005

(54) FLUORESCENT CREATININE ASSAY

(75) Inventors: James P. Albarella, Granger, IN (US); Robert P. Hatch, Elkhart, IN (US)

(73) Assignee: Bayer Corporation, East Walpole, MA (US)

(*) Notice: Subject to any disclaimer, the term of this patent is extended or adjusted under 35 U.S.C. 154(b) by 10 days.

(21) Appl. No.: 10/335,718

(22) Filed: Jan. 2, 2003

(65) Prior Publication Data

US 2004/0132200 A1 Jul. 8, 2004

(51) Int. Cl.[7] .............................................. G01N 33/00
(52) U.S. Cl. ........................ 436/98; 436/80; 436/135; 436/164; 436/169; 436/172; 436/800; 436/108; 422/55; 422/56; 422/82.08
(58) Field of Search ............................. 436/98, 73, 74, 436/80, 135, 164, 166, 169, 172, 800, 904, 108; 422/55, 56, 82.05, 82.08

(56) References Cited

U.S. PATENT DOCUMENTS

| | | | |
|---|---|---|---|
| 4,384,042 A | 5/1983 | Miike et al. | 435/25 |
| 5,173,431 A | 12/1992 | Pugia et al. | 436/86 |
| 5,374,561 A | 12/1994 | Pugia | 436/98 |
| 5,399,498 A | 3/1995 | Pugia | 436/86 |
| 5,527,708 A | 6/1996 | Blass | 436/98 |
| 5,662,867 A | 9/1997 | Pugia et al. | 422/56 |
| 5,702,955 A | 12/1997 | Pugia | 436/135 |
| 5,733,787 A | 3/1998 | Messenger et al. | 436/98 |
| 5,958,786 A | 9/1999 | Munkholm | 436/98 |
| 6,001,656 A | 12/1999 | Cast et al. | 436/98 |
| 6,074,881 A * | 6/2000 | Cast et al. | 436/74 |
| 6,210,971 B1 | 4/2001 | Messenger et al. | 436/98 |
| 6,228,602 B1 | 5/2001 | Pugia | 435/7.32 |

FOREIGN PATENT DOCUMENTS

WO        WO 00/11205        3/2000        ............ C12Q/1/00

OTHER PUBLICATIONS

Uchiyama, Seiichi; Santa, Tomofumi and Kazuhiro, Imai, "Semi–emperical PM3 calculation reveals the relationship between the fluorescence characteristics of 4, 7–disubstituted benzofurazan compounds, the LUMO energy and the dipole moment directed from the 4– to the 7–position," J. Chem. Soc., Perkins Trans. 2, 1999, 569–576.

Translation of Description and Claims of DE 19932380A1.

Shiga, Masanobu; Sasamoto, Kazsumi; Aoyama, Masaaki; Takagi, Makoto and Ueno, Keiyu, "Fluorescence Detection of DNA Using A Novel Peroxidase Substrate, 4–(4–Hydroxyphenylcarbamoyl)butanoic Acid," Analytical Sciences, Aug. 1995, vol. II, 591–595.

Sakuragawa, Akio; Taniai, Tetsuyuki and Okutani, Tadao, "Fluorometric determination of microamounts of hydrogem peroxide with an immobilized enzyme prepared by coupling horseradish peroxidase to chitosan beads," Elsevier Science B.V. © 1998, 10 pgs.

Li, Yuan–Zong and Townshend, Alan, "Comparative study of some synthesised and commercial fluorogenic substrates for horseradish peroxidase and its mimetic enzyme hemin a flow injection method," Elsevier Science B.V. © 1997, 10 pgs.

Brotea, G.P. and Tribert, R.J., "Fluorometric Determination of Hydrogen Peroxide Using Resorufin and Peroxidase," Adcademic Press, Inc. © 1968, pp 368–376.

"Ultrasensitive Fluorgenic Enzyme Assays," Molecular Probes, Sci–Finder, Feb. 2, 2001, 3 pages.

Mekler, V.M. and Bystyak, S.M., "Application of o–phenylenediaminc as a fluorogenic substrate in peroxidase–mediated enzyme–linked immunosorbent assay," Elsevier Science Publishers B.V. © 1992, pp. 359–363.

Nohta, Hitoshi; Watanabe, Tomohiro; Nagaoka, Hiroaki and Ohkura, Yosuke, "Assay for Peroxidase Using 1, 2–Diarylethylenediamines and Catechol Compounds as Fluorogenic Substrates," Analyticial Sciences, Jun. 1991, vol. 7, 437–441.

Whitaker, James E.; Moore, Patrick L.; Haugland, Rosaria P. and Haugland, Richard P., "Dihydrotetramethylrosamine: A Long Wavelength, Fluorogenic Peroxidase Substrate Evaluated In Vitro and in a Model Phagocyte," Biochemical and Biophysical Research Communications, © 1991 by Academic Press, Inc., vol. 175, No. 2, Mar. 15, 1991, pp 387–393.

Instructions QuantaBlue™ Fluorogenic Substrate Kit and QualtaBlue™ NS/K Fluorogenic Peroxidase Substrate Kit, Pierce, 2 pages.

Instructions FluoroBlot™ Peroxidase Substrate, Pierce, 4 pages.

Chen, Xiao–Lan; Li, Dong–Hui; Yang, Huang–Hao; Zhu, Qing–Zhi; Zheng, Hong and Xu Jin–Goru, "Study of tetra-–substituted amino aluminum phthalocyanine as a new red–region substrate for the fluorometric determination of peroxidase and hydrogen peroxide," Elsevier Science B.V. © 2001, 8 pages.

Chen, Xiao–Lan; Li, Dong–Hui; Yang, Huang–Hao; Zhu, Qing–Zhi; Zheng, Hong and Xu, Jin–Gou, "A new red–region substrate, tetra–substituted amino aluminum phthalocyanine, for the Fluorimetric determination of $H_2O_2$ catalyzed by mimetic peroxidases," The Royal Society of Chemistry 2001, Analyst, pp. 523–527.

Meyer et al., Angew Chem 2000.

* cited by examiner

Primary Examiner—Maureen M. Wallenhorst
(74) Attorney, Agent, or Firm—Jenkens & Gilchrist

(57) ABSTRACT

A method of detecting creatinine in body fluids using an indicator which produces a fluorescent response when oxidized in the presence of a copper[II]/creatinine complex. A preferred indicator is 4-(1-methylhydrazino)-7-nitro benzooxadiazole (MNBDH).

33 Claims, 1 Drawing Sheet

FLUORESCENT CREATININE ASSAY

BACKGROUND OF THE INVENTION

This invention relates generally to the determination of the amount of creatinine in urine or other bodily fluids. More particularly, the invention relates to an improvement in creatinine assays in which copper complexes with creatinine and then acts as a oxidant for a indicator, for example one in which a color change provides an indication of the creatinine concentration.

Creatinine is the end metabolite when creatine becomes creatine phosphate and is used as an energy source for muscle contraction. The creatinine product is filtered in the kidneys and excreted into the urine. The amount of the creatinine in the urine provides an indicator useful for diagnosing muscle diseases or kidney diseases. Various tests have been used for measuring the concentration of creatinine, such as those discussed in the patents related to the present invention and discussed below.

In a series of US Patents, Miles, Inc. and later the Bayer Corporation, disclosed methods of analysis that employed copper complexes serving as pseudoperoxidases for oxidizing redox indicators such as 3,3',5,5'-tetramethylbenezidine (TMB). The earliest of these was U.S. Pat. No. 5,173,431 in which a copper/protein complex was used and an ionizable phosphate was included in the system to prevent interference by components in the biological fluid being tested. In U.S. Pat. No. 5,374,561, it was shown that a complex of $Cu^{II}$ with creatinine was capable of oxidizing a redox indicator to provide a measure of the amount of creatinine present in a urine sample. The sample was brought into contact with a test strip containing cupric ions, a hydroperoxide, and a redox indicator. A set of reactions was postulated in which the creatinine in the sample was complexed with the cupric ions and the complex oxidized the indicator to a colored form. The reduced copper/creatinine complex was reoxidized to the cupric form by the hydroperoxide. Improvements in the method of the '561 patent were disclosed in U.S. Pat. Nos. 5,733,787; 6,001,656; and 6,210,971. The improved methods reduce interference of components in the sample and extend the useful shelf life of the test strips in order that more accurate results can be obtained.

Other methods of detecting of creatinine have been established. Some of these involve the use of fluorescent materials to detect the presence of creatinine, rather than by developing a color. One such method is disclosed in U.S. Pat. No. 5,958,786 in which a fluorescent dye, e.g. acridine orange, was used to detect ammonia produced by the reaction of creatinine with the enzyme creatinine deiminase. In U.S. Pat. No. 5,527,708 creatinine was reacted with 3,5-dinitrobenzoate to produce a fluorescent material. In neither of these methods was a copper/creatinine complex formed.

While the use of copper/creatinine complexes has been shown to be successful in measuring creatinine in urine samples, further improvement is, as always, sought by those skilled in this art. Since current methods use enzymes, which are more costly and unstable, or are colorometric and are optically interfered in serum. It would be preferred to use a less costly method or, if the application is in serum, use one that is free from optical interferences.

Thus, the present inventors continued investigation of creatinine measurement and discovered the new method which will be described in detail below. In general, the colorimetric indicator is replaced by a fluorescent indicator, which is especially useful in measurement of creatinine in blood and other bodily fluids.

Fluorescent indicators have been used for analytes that have an oxidase specific toward them such as cholesterol or glucose. In one example, 4-(1-methylhydrazino)-7-nitrobenzooxadiazole (MNBDH) was used as a fluorogenic peroxidase indicator to produce fluorescence when oxidized by hydrogen peroxide, which had been generated by the reaction of glucose with glucose oxidase. See Meyer, J.; Buldt, A.; Vogel, M. Karst, U., Angew. Chem. Int. Ed. 2000, 39(8) 14 53 and Ger. Patent 199 32 380 A 1, 2000.

Although measurement of the creatinine concentration in urine has been the focus of the patents discussed above, creatinine also is found in blood. Serum and plasma concentrations of creatinine elevate in extensive renal disease, especially from decreased glomular filtration.

A single random serum creatinine measurement may be used as an indicator of renal failure. However, a more sensitive test for measuring glomular filtration is the creatinine clearance test. In this test, the serum creatinine concentration is used in conjunction with the measurement of creatinine in the precisely timed (usually 24 hr) urine sample to estimate the Glomular Filtration Rate (GFR). Creatinine clearance is used to follow the clinical course and therapeutic response in acute glomerulonephritis, to discriminate between acute glomular disease vs. chronic structural damage and as a measurement of overall renal function. Presently, creatinine in blood is measured by variations of the Jaffe method, which is sensitive to blood interferants such as glucose, ascorbate, uric acid, keto acids, pyruvate, proteins cephalosporins drugs and background signal. Alternatively, enzymatic methods are also used, which are expensive and suffer from enzyme instabilities. Thus, extension of the specific yet less complex creatinine complex method would constitute an improvement in the art of creatinine detection. The present inventors have found the new method which is described in detail below.

SUMMARY OF THE INVENTION

In one aspect, the invention is a new method for the detection of creatinine in blood or other bodily fluids where an indicator providing a color change is not suitable. In the new method a sample of the bodily fluid containing creatinine is contacted with a reagent system comprising cupric ions, a hydroperoxide and an indicator which produces a fluorescent response when oxidized by a peroxidase or pseudoperoxidase and hydrogen peroxide. In the invention, such indicators are those having the formula:

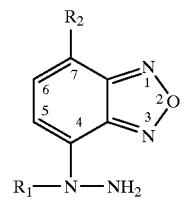

where:
  $R_1$ is $C_1$–$C_7$
  $R_2$ is $NO_2$, $R_3NHSO_2$, $(R_3)_2NSO_2$
  $R_3$ is hydrogen, alkyl, substituted alkyl, phenyl, substituted phenyl.

The indicator is a member of the group consisting of 4-(1-alkylhydrazino)-7 substituted benzooxadiazoles where the 7 substituent, with oxidatively cleaved 4-hydrazino group generates a fluorescent product. Common examples of 7-substituents are nitro, and sulfonamides. J. Chem. Soc., Perkin Trans. 2, 1999, 569–76). Most preferred because of its easy accessibility is 4-(N-methylhydrazino)-7-nitrobenzooxadiazole (MNBDH). MNBDH corresponds to a compound where $R_1$ is methyl and $R_2$ is nitro.

In another aspect, the invention is an improvement in the method of detecting creatinine by contacting a sample containing creatinine with a reagent system comprising cupric ions, a hydroperoxide and an indicator, in which the indicator is one which provides a fluorescent response when oxidized in the presence of a peroxidase or pseudoperoxidase and hydrogen peroxide. The indicator is a member of the group consisting of 4-(1-alkylhydrazino)-7-substituted benzooxadiazoles according to the above formula where the 7 substituent, with the cleaved 4-hydrazino, group, generates a fluorescent 4-alkyl amino-7-substituted benzooxadiazole. Most preferred, because of its easy accessibility, is MNBDH.

In still another aspect, the invention is a reagent system for use in an assay for creatinine in fluids, particularly blood or other bodily fluids.

DESCRIPTION OF THE PREFERRED EMBODIMENTS

Copper$^{II}$ Creatinine Complexes

Figure 1:
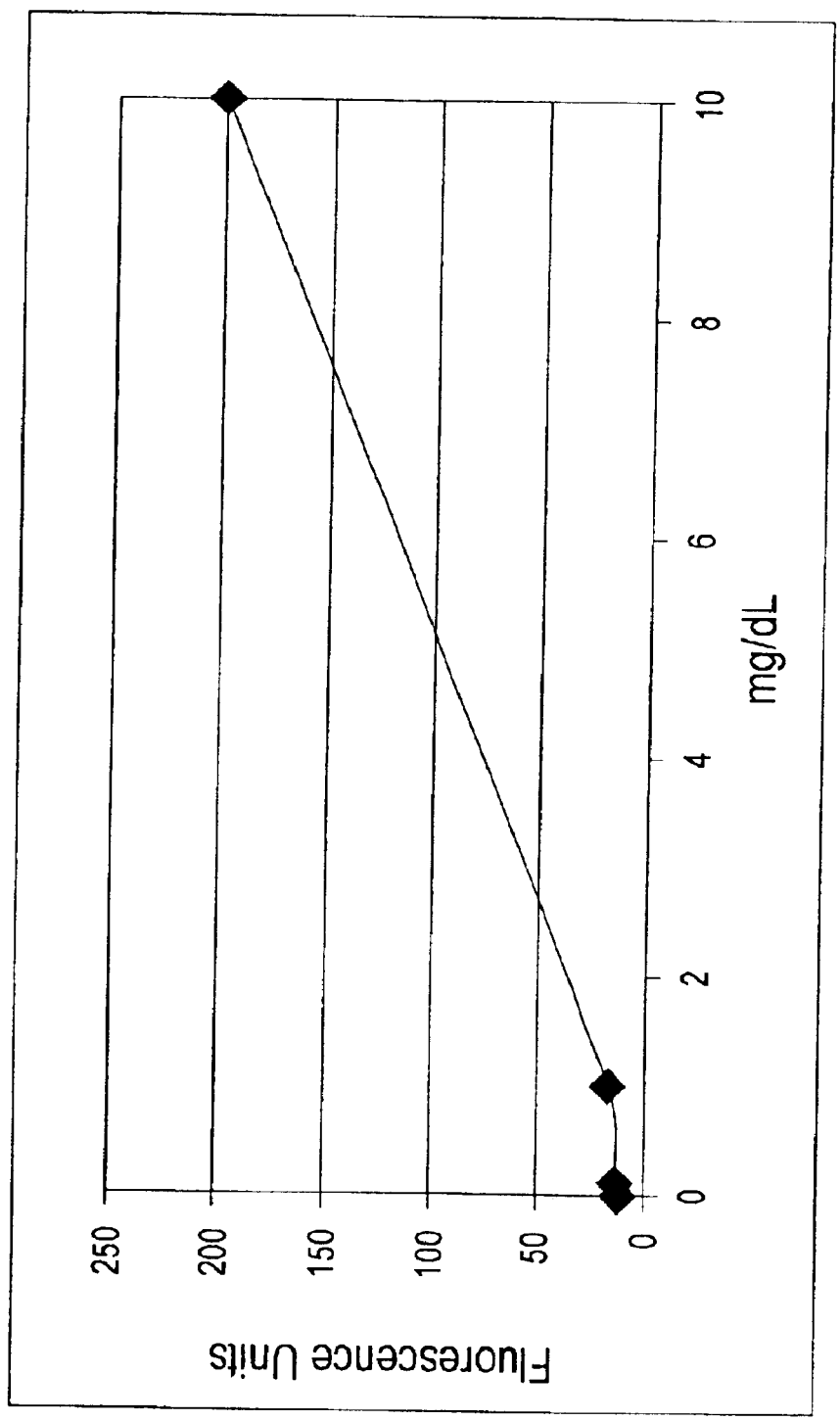
FIG. 1 is a graph of the response of a fluorescent indicator to the concentration of creatinine in a sample as described in Example 1.

In U.S. Pat. No. 5,374,561, a set of reactions was postulated that accounted for the discovery that cupric compounds could complex with creatinine and thereafter act as a pseudoperoxidase in the oxidation of a chromophoric indicator, such as 3,3',5,5'-tetramethylbenzidine (TMB). The color developed by oxidation of the indicator provided a measure of the concentration of the creatinine present in the sample being tested. For example, cupric ions were supplied as cupric sulfate plus citric acid, complexed with creatinine and then oxidized TMB while being reduced to copper (I) creatinine, which was reoxidized to the cupric form by diisopropylbenzene dihydroperoxide (DBDH).

It was stated in the '561 patent that the source of cupric ions could be any soluble copper salt whose anion does not detrimentally interact with the reaction for the colorimetric detection of creatinine. In the present invention the same considerations apply, except that the indicator provides a fluorescent response rather than a color change. Suitable copper salts include the sulfate, acetate, chloride, phosphate and hydroxide. As in the '561 patent copper salts whose anions bind too strongly to the copper interfere with the formation of the copper-creatinine complex should be avoided, for example, thiocyanate, sulfide and complexing agents such as EDTA. Copper citrate is a preferred source of cupric ions since it best allows creatinine to form a peroxidatively active complex with copper and has a low blank reactivity.

Various hydroperoxides may be used to reoxidize the copper$^I$creatinine complex. They include but are not limited to diisopropylbenzene dihydroperoxide, and cumene hydroperoxide. An excess of the hydroperoxide relative to the copper ions is supplied in order to facilitate the reaction rate.

Fluorescent Indicators

While chromophoric indicators were suitable for use in analysis of urine, a color change in response to oxidation is not always detectable when other fluids are being analyzed. Thus, in the present invention fluorescent indicators are used instead. In general the fluorescent indicators will be of the 4-(1-alkylhydrazino)-7-substituted-benzooxadiazoles-type (sometimes also called benzofurazans).

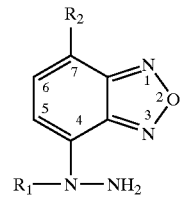

where:
$R_1$ is $C_1$–$C_7$
$R_2$ is $NO_2$, $R_3NHSO_2$, $(R_3)_2NSO_2$
$R_3$ is hydrogen, alkyl, substituted alkyl, phenyl, or substituted phenyl.

Of these, because of ease of availability, 4-(1-methylhydrazino)-7-nitrobenzooxadiazole (MNBDH) is used to demonstrate the invention. Examples of potential 7-substituents can be found in J. Chem Soc., Perkin Trans. 2, 1999 569–76 and 1999 2525–2532. The concentration of the indicator used will depend upon the desired reaction rate and background.

In the above formula, the alkyl group $R_1$ typically is $C_7$ or smaller, but it may be substituted to provide desired solubility or to immobilize the indicator molecule.

$R_3$ will be an alkyl or a phenyl group, either of which may be substituted with functional groups to provide the desired solubility or optical properties. For example, $R_3$ could be a methyl or ethyl group, but the compound would be more lipophilic if $R_3$ had a longer carbon chain, e.g., decyl or dodecyl. Alternatively, the solubility of the compounds in water would be increased when $R_3$ is for example, 2-sulfoethyl($-O_3SCH_2CH_2-$), carboxymethyl($-O_2CCH_2-$), or dimethylaminopropyl [$(CH_3)_2N(CH_2)_3$]. Both lipophilicity and water solubility would be increased when $R_3$ is an n-(ethyleneglycol)ethyl [$(CH_3-,CH_3CH_2-$, or $H-O(CH_2CH_2O)_nCH_2CH_2$]. Chain lengths could be chosen to further adjust the properties of $R_3$. Also, other substituents could be included that would modify $R_3$'s properties, including, but not limited to, hydroxyl, amino, and trialkylammonio.

When $R_3$ is a phenyl group lipophilicity is increased. Functional groups such as methoxy, nitro, chloride, bromide, or iodide in the 2, 3, or 4 positions on the phenyl ring could change the fluorescent properties. Water solubility could be increased by including substituents such as sulfo, carboxy, dimethylamino, trialkylammonio, and n-(ethylene glycol) ethyl.

FIG. 1 illustrates the response of MNBDH in a series of tests in which the concentration of creatinine was varied, using the conditions of Example 1 below. When the concentration of creatinine was zero, the fluorescence measured did not significantly change during the assay. However, with the relatively low concentration of 0.1 mg/dL of creatinine a slight response was measured. Further increases in creatinine concentration to 1 mg/dL and 10 mg/dL provided readily measured signals. Since the typical concentration of creatinine in blood is expected to be about 0.2 to 10 mg/dL, it is evident that the fluorescent indicator provides a strong response to oxidation by the copper$^{II}$ creatinine complex, making it suitable for measurement of blood and other bodily fluids where a chromophoric indicator is less satisfactory.

Applications

The method of the invention will be useful in assays of various bodily fluids, particularly, but not limited to serum and blood. While the method can be used manually, that is, one could add cupric compounds, a hydroperoxide and a fluorescent indicator to a sample of blood and then measure the fluorescence developed in a cuvette, it is also possible to use other techniques, such as test strips having the reagents added.

It is believed that test strips will be particularly useful for measuring creatinine in serum where optical interferences are the greatest. For example, a strip of filter paper could be dipped into a solution of the cupric compounds along with other compounds to bind potentially interfering materials in the sample, buffers and the like. Then, after drying the first solution on the strip of filter paper, it could be dipped into a second solution containing the fluorescent indicator and the hydroperoxide and dried a second time.

Another application for the method of the invention is found in automated analyzers, such as the blood analyzers described in WO 00/11205. For example, the reagents could be dissolved in a solution containing a soluble, transparent, water-permeable polymer. The resulting solution could be stripped onto a backing and dried to provide a reagent pad. Passing a serum sample over the membrane allows the creatinine to absorb into the membrane and react to generate a fluorescent signal to be measured by a suitable system, such as that illustrated in WO 00/11205.

EXAMPLE 1

An aqueous solution was prepared containing 0.84 mM $Cu^{II} SO_4$ 1.6 mM citrate as citric acid hydrate and 25 mM succinate as succinic acid and adjusted to a pH of 7 by adding sodium hydroxide. To the resulting solution was added 200 µL of 2.2 mg/mL of diisopropyl benzene dihydroperoxide in water containing 12.2 mg/mL of hydroxypropyl cyclodextrin, 0.5 mL of aqueous creatinine solution 20 µL of 1 mg/mL MNBDH in acetonitrile. The fluorescence produced was measured with a Perkin Elmer LS50B fluorimeter after 5 minutes. As seen in FIG. 1, the measured fluorescence (relative units) increased with increased creatinine concentration.

What is claimed is:

1. A method for the detection of creatinine in fluids comprising contacting a sample of said fluid with a reagent system comprising cupric ions, a hydroperoxide and an indicator which produces a fluorescent response when oxidized in the presence of a pseudoperoxidase, wherein said indicator is a 4-(1-alkylhydrazino)-7-substituted benzooxadiazole having the formula:

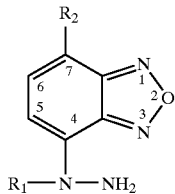

where:
$R_1$ is $C_1$–$C_7$
$R_2$ is $NO_2$, $R_3NHSO_2$, $(R_3)_2NSO_2$
$R_3$ is hydrogen, alkyl, substituted alkyl, phenyl, substituted phenyl.

2. A method of claim 1, wherein said indicator is 4-(1-methylhydrazino)-7-nitro-benzooxadiazole (MNBDH).

3. A method of claim 1 wherein said reagent system further comprises citric acid.

4. A method of claim 1 wherein said cupric ions are supplied by a member of the group consisting of copper sulfate, copper chloride, copper phosphate, and copper hydroxide.

5. A method of claim 1 wherein said hydroperoxide is diisopropylbenzene dihydroperoxide or cumene hydroperoxide.

6. A method of claim 1 wherein said reagent system is placed on a test strip.

7. A method of claim 1 wherein said alkyl or said phenyl of $R_3$ are substituted to provide predetermined solubility and/or optical properties.

8. A method of claim 7 wherein said phenyl is substituted with at least one group selected from the group consisting of methoxy, nitro, chloride, bromide, or iodide to provide predetermined fluorescent properties.

9. A method of claim 7 wherein said phenyl is substituted with at least one substituent selected from the group consisting of sulfo, carboxy, dimethylamino, trialkylammonio, and ethylene glycol to increase water solubility.

10. A method of claim 7 wherein said alkyl is methyl, ethyl, or a longer alkyl chain to increase lipophilicity.

11. A method of claim 7 wherein said alkyl is selected from the group consisting of 2-sulfoethyl, carboxymethyl, and dimethylaminopropyl to increase water solubility.

12. A method of claim 7 wherein said alkyl is an n-(ethylene glycol)ethyl to increase both lipophilicity and water solubility.

13. A method of claim 7 wherein said alkyl is substituted with at least one member of the group consisting of hydroxyl, amino, and trialkylammonio.

14. In a method for the detection of creatinine in blood or other bodily fluids wherein a sample of said fluids is contacted with a reagent system comprising cupric ions, a hydroperoxide and an indicator, the improvement comprising the use of an indicator which produces a fluorescent response when oxidized in the presence of a pseudoperoxidase, wherein said indicator is a 4-(1-alkylhydrazino-7-substituted benzooxadiazole having the formula:

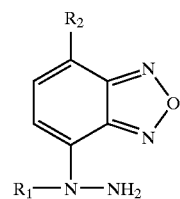

where:
$R_1$ is $C_1$–$C_7$
$R_2$ is $NO_2$, $R_3NHSO_2$, $(R_3)_2NSO_2$
$R_3$ is hydrogen, alkyl, substituted alkyl, phenyl, substituted phenyl.

15. The method of claim 14 wherein said indicator is 4-(N-methylhydrazino)-7-nitrobenzooxadiazole (MNBDH).

16. The method of claim 14 wherein said reagent system further comprises citric acid.

17. The method of claim 14 wherein said cupric ions are supplied by a member of the group consisting of copper sulfate, copper chloride, copper phosphate, and copper hydroxide.

18. The method of claim 14 wherein said hydroperoxide is diisopropylbenzene dihydroperoxide or cumene hydroperoxide.

19. The method of claim 14 wherein said reagent system is placed on a test strip.

20. A method of claim 14 wherein said alkyl or said phenyl of $R_3$ are substituted to provide predetermined solubility and/or optical properties.

21. A method of claim 20 wherein said phenyl is substituted with at least one group selected from the group consisting of methoxy, nitro, chloride, bromide, or iodide to provide predetermined fluorescent properties.

22. A method of claim 20 wherein said phenyl is substituted with at least one substituent selected from the group consisting of sulfo, carboxy, dimethylamino, trialkylammonio, and ethylene glycol to increase water solubility.

23. A method of claim 20 wherein said alkyl is methyl, ethyl, or a longer alkyl chain to increase lipophilicity.

24. A method of claim 20 wherein said alkyl is selected from the group consisting of 2-sulfoethyl, carboxymethyl, and dimethylaminopropyl to increase water solubility.

25. A method of claim 20 wherein said alkyl is an n-(ethylene glycol) ethyl to increase both lipophilicity and water solubility.

26. A method of claim 20 wherein said alkyl is substituted with at least one member of the group consisting of hydroxyl, amino, and trialkylammonio.

27. An assay for creatinine in fluids in which assay a fluid sample is contacted with a reagent system comprising cupric ions, a hydroperoxide, and an indicator which produces a fluorescent response when oxidized in the presence of a pseudoperoxide, wherein said indicator is a 4-(1-alkylhydrazino)-7-substituted benzooxadiazole having the formula:

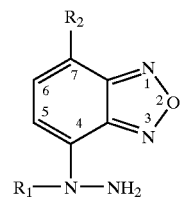

where:

$R_1$ is $C_1$–$C_7$ $R_2$ is $NO_2$, $R_3NHSO_2$, $(R_3)_2NSO_2$ $R_3$ is hydrogen, alkyl, substituted alkyl, phenyl, substituted phenyl.

28. An assay of claim 27 wherein said indicator is 4-(N-methylhydrazino)-7-nitrobenzooxadiazole (MNBDH).

29. An assay of claim 27 further comprising citric acid.

30. An assay of claim 27 wherein said cupric ions are supplied by a member of the group consisting of copper sulfate, copper chloride, copper phosphate, and copper hydroxide.

31. An assay of claim 27 wherein said hydroperoxide is diisopropylbenzene dihydroperoxide or cumene hydroperoxide.

32. An assay of claim 27 wherein said reagent system further comprises a substrate.

33. An assay of claim 32 wherein said substrate is a test strip.

* * * * *